United States Patent
Imura et al.

(10) Patent No.: US 9,533,926 B2
(45) Date of Patent: Jan. 3, 2017

(54) METHOD FOR PRODUCING 2-CHLORO-1,3,3,3-TETRAFLUOROPROPENE

(71) Applicant: Central Glass Company, Limited, Ube-shi, Yamaguchi (JP)

(72) Inventors: Hideaki Imura, Fujimino (JP); Naoto Takada, Saitama (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

(21) Appl. No.: 14/809,376

(22) Filed: Jul. 27, 2015

(65) Prior Publication Data

US 2016/0023968 A1 Jan. 28, 2016

(30) Foreign Application Priority Data

Jul. 28, 2014 (JP) ................................. 2014-152523
Jun. 4, 2015 (JP) ................................. 2015-113564

(51) Int. Cl.
*C07C 17/25* (2006.01)
*B01J 31/02* (2006.01)

(52) U.S. Cl.
CPC ............ *C07C 17/25* (2013.01); *B01J 31/0271* (2013.01); *B01J 2231/76* (2013.01); *B01J 2531/002* (2013.01); *Y02P 20/582* (2015.11)

(58) Field of Classification Search
CPC ..................................................... C07C 17/25
See application file for complete search history.

(56) References Cited

U.S. PATENT DOCUMENTS

| 3,499,089 | A | 3/1970 | Regan |
| 6,548,719 | B1 * | 4/2003 | Nair ........................ C07C 17/04 570/157 |
| 9,035,112 | B2 | 5/2015 | Imura et al. |
| 2010/0204529 | A1 | 8/2010 | Terada et al. |
| 2011/0288346 | A1 * | 11/2011 | Poss ........................ C07C 17/04 570/154 |
| 2012/0302803 | A1 | 11/2012 | Yamashita et al. |
| 2013/0274528 | A1 | 10/2013 | Sharratt et al. |
| 2015/0011805 | A1 | 1/2015 | Okamoto et al. |
| 2015/0038749 | A1 * | 2/2015 | Imura ........................ C07C 17/25 570/155 |

FOREIGN PATENT DOCUMENTS

| CN | 1589248 A | 3/2005 | |
| CN | 101563308 A | 10/2009 | |
| CN | 101796002 A | 8/2010 | |
| CN | 102762524 A | 10/2012 | |
| JP | 2013-103890 A | 5/2013 | |
| JP | WO 2014046250 A1 * | 3/2014 | ............. C07C 17/25 |

OTHER PUBLICATIONS

WO 2014046250 A1, Mar. 2014, pp. 1-7.*
Haszeldine, et al. "Polyfluoroalkyl Derivatives of Silicon. Part XIV[1]. Reaction of Tri-chlorosilane with 1,3,3,3-Tetrafluoropropene and 2-Chloro-1,3,3,3-tetra-fluoropropene", Journal of the Chemical Society, Dalton, Feb. 1975, vol. 1975, No. 21, pp. 2292-2294 (Three (3) pages).
Chinese-language Office Action issued in counterpart Chinese Application No. 201540151162.1 dated Sep. 2, 2016 (Six (6) pages).

* cited by examiner

*Primary Examiner* — Jafar Parsa
*Assistant Examiner* — Medhanit Bahta
(74) *Attorney, Agent, or Firm* — Crowell & Moring LLP

(57) ABSTRACT

A production method of 2-chloro-1,3,3,3-tetrafluoropropene (1224) according to the present invention includes bringing 2,3-dichloro-1,1,1,3-tetrafluoropropane (234da) into contact with an inorganic base having a pKa of 4.8 or greater in an aqueous medium in the presence of a phase transfer catalyst. Preferably, the inorganic base has a pKa of 10 or greater. Further, the phase transfer catalyst is preferably at least one selected from the group consisting of tetrabutylammonium bromide, methyltri-n-octylammonium chloride, benzyltrimethylammonium chloride and tetraethylammonium chloride. It is possible by this method to selectively produce 1224 from 234da.

7 Claims, No Drawings

METHOD FOR PRODUCING 2-CHLORO-1,3,3,3-TETRAFLUOROPROPENE

FIELD OF THE INVENTION

The present invention relates to a method for producing 2-chloro-1,3,3,3-tetrafluoropropene. Herein, 2-chloro-1,3,3,3-tetrafluoropropene is useful as a cleaning agent, a coolant, a heating medium for a heat pump, a high-temperature working fluid or the like.

BACKGROUND OF THE INVENTION

In place of specific chlorofluorocarbons designated as strong ozone-depleting substances by the Montreal Protocol agreed in Canada in 1987, various alternative fluorocarbons with less fear of ozone depletion are synthesized and used. In recent years, the alternative chlorofluorocarbons are also required to show a shorter life in the air and less fear of global warming.

It is known that 2-chloro-1,3,3,3-tetrafluoropropene, which has a double bond in its molecule, gets quickly decomposed by reaction of the double bond with OH radial etc. in the air and thereby shows a low global warming potential and less fear of global warming. There exist trans and cis geometric isomers of 2-chloro-1,3,3,3-tetrafluoropropene. Hereinafter, the trans and cis isomers of 2-chloro-1,3,3,3-tetrafluoropropene is sometimes referred to as "1224E" and "1224Z", respectively; and 2-chloro-1,3,3,3-tetrafluoropropene is sometimes simply referred to as "1224" in the case where there is no need to distinguish the trans and cis isomers or in the case where it refers to a mixture of the trans and cis isomers. The boiling point of 1224E is 23° C., whereas the boiling point of 1224Z is 17° C. Both of 1224E and 1224Z have a boiling point in the vicinity of room temperature (about 20° C.) and can suitably be used as blowing agents, solvents, coolants, working fluids or the like.

In the case of using 1224 as a blowing agent for a heat insulating material, low-boiling 1224Z is suitably usable for a heat insulating material in a refrigerator; and high-boiling 1224E is suitably usable for a heat insulating material in a building because of its good handling properties.

As the boiling point of 1224 is in the vicinity of room temperature, 1224 can also suitably be used as a heating medium for a heat pump or a high-temperature working fluid. In the case of using 1224 as a high-temperature working fluid for a heat pump, the coefficient of performance (COP) of the heat pump, which indicates cooling/heating capacity per 1 kW of power consumption, and the heat transfer capacity of the heat pump in freezing cycles etc. vary with even a slight difference in boiling point of the working fluid. In the case of using 1224 as a high-temperature working fluid, the suitable boiling point of the working fluid varies depending on the conditions of thermal cycles. It is thus preferable to appropriately select and use either the trans isomer (1224E) or the cis isomer (1224Z) according to the purpose of use.

In the following Patent Documents 1 and 2 and Non-Patent Document 1, there are disclosed processes of forming 1224.

Patent Document 1 discloses a process for purifying a (E)-1-chloro-3,3,3-trifluoropropene composition, which contains at least hydrogen fluoride and 2-chloro-1,1,1,3,3-pentafluoropropane, by contact with a weak base. More specifically, this process includes the step of bringing trans-1-chloro-3,3,3-trifluoropropane (sometimes abbreviated as "1233E") containing hydrogen fluoride and 2-chloro-1,1,1,3,3-pentafluoropropane (sometimes abbreviated as "235da") as a trace impurity into contact with the weak base so as to remove hydrogen fluoride and 235da and obtain 1233E as a purified product without forming 1224.

Non-Patent Document 1 discloses, as a specific synthesis example of 1224, a method for forming 2,3-dichloro-1,1,1,3-tetrafluoropropane (sometimes referred to as "234da") by photochlorination of 1,3,3,3-tetrafluoropropene (sometimes referred to as "1234"), and then, forming 1224 by dehydrochlorination of 234da in a potassium hydroxide solution. Herein, 234da is a hydrochlorofluorocarbon represented by $CF_3CHClCHClF$.

Further, Patent Document 2 discloses a method for forming 235da as a raw material of 1224.

PRIOR ART DOCUMENTS

Patent Document 1: Japanese Laid-Open Patent Publication No. 2013-103890
Patent Document 2: U.S. Pat. No. 3,499,089
Non-Patent Document 1: Journal of the Chemical Society, Dalton Transactions: Inorganic Chemistry, Vol. 1975, No. 21, P. 2292-2294 (1975)

SUMMARY OF THE INVENTION

It is an object of the present invention to provide a method for efficiently producing 2-chloro-1,3,3,3-tetrafluoropropene (1224) by contact of 2,3-dichloro-1,1,1,3-tetrafluoropropane (234da) with an inorganic base while suppressing the generation of a by-product.

As shown in the following reaction scheme, 2,3-dichloro-1,1,1,3-tetrafluoropropane (234da) is dehydrochlorinated with a base to form 2-chloro-1,3,3,3-tetrafluoropropene (1224). The method disclosed in Non-Patent Document 1 gives 1224 by dehydrochlorination of 234da and gives 1,2-dichloro-3,3,3-trifluoropropene ($CF_3CCl=CHCl$; sometimes referred to as "1223") by dehydrofluorination of 234da as shown in the following scheme. It is discussed in page 2294 of Non-Patent Document 1 that the yield of 1224 by dehydrochlorination of 234da is 69%, the rest being assumed to be 1223 as a by-product. Less by-production of 1223 is preferable in the case where only 1224 is desired by a manufacturer.

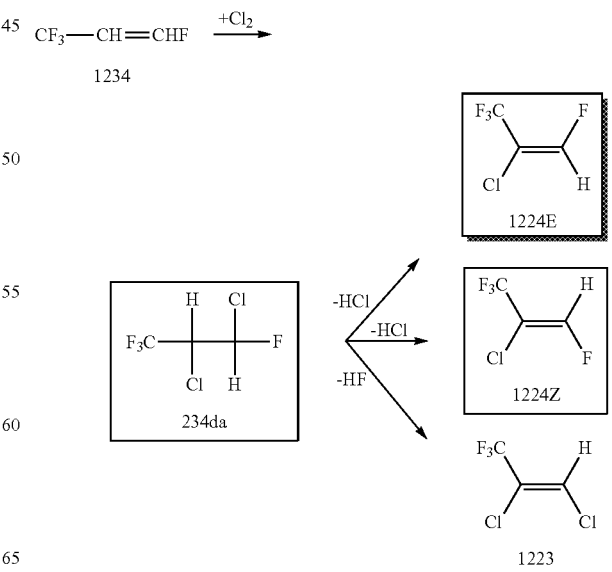

As mentioned above, there is a problem that it is impossible to efficiently obtain only 1224 due to by-production of 1223 during the formation reaction of 1224 by contact of 234da as the organic reactant material with the inorganic base in the aqueous solution.

The present inventors have however found as a result of extensive researches that, by bringing 2,3-dichloro-1,1,1,3-tetrafluoropropane (234da) as an organic reactant material into contact with an inorganic base in an aqueous medium in the presence of a phase transfer catalyst, it is possible to suppress the generation of 1,2-dichloro-3,3,3-trifluoropropene (1233) as a by-product and efficiently produce 2-chloro-1,3,3,3-tetrafluoropropene (1224). The present invention is based on such a finding.

In the present invention, the term "aqueous medium" refers to a liquid medium that contains water as an essential component and may optionally contain an organic solvent.

When the organic reactant material 234da is just brought into contact with the inorganic base in the aqueous medium, the dehydrofluorination of 234da is likely to proceed so that the selectivity of formation of 1224 becomes lowered due to the generation of 1223 as the by-product. The present inventors have found that, when this contact reaction is performed in the presence of the phase transfer catalyst, it is surprisingly possible to suppress the generation of 1223 as the by-product and increase the selectivity of formation of 1224 by dehydrochlorination, and then, have accomplished a production method of 1224 according to the present invention.

Namely, the present invention includes the following inventive features 1 to 6.

Inventive Aspect 1

A production method of 2-chloro-1,3,3,3-tetrafluoropropene (1224), comprising: bringing 2,3-dichloro-1,1,1,3-tetrafluoropropane (234da) into contact with an inorganic base having a pKa of 4.8 or greater in an aqueous medium in the presence of a phase transfer catalyst.

Inventive Aspect 2

The production method according to Inventive Aspect 1, wherein the inorganic base has a pKa of 10 or greater.

Inventive Aspect 3

The production method according to Inventive Aspect 2, wherein the inorganic base is either sodium hydroxide or potassium hydroxide.

Inventive Aspect 4

The production method according to Inventive Aspect 1, wherein the phase transfer catalyst is a quaternary ammonium salt.

Inventive Aspect 5

The production method according to Inventive Aspect 4, wherein the phase transfer catalyst is a quaternary ammonium salt of 8 to 50 carbon atoms.

Inventive Aspect 6

The production method according to Inventive Aspect 5, wherein the phase transfer catalyst is at least one selected from the group consisting of tetrabutylammonium bromide, methyltri-n-octylammonium chloride, benzyltrimethylammonium chloride and tetraethylammonium chloride.

In the production method of 2-chloro-1,3,3,3-tetrafluoropropene (1224) according to the present invention, 2,3-dichloro-1,1,1,3-tetrafluoropropane (234da) as the organic reactant material is brought into contact with the inorganic base in the aqueous medium in the presence of the phase transfer catalyst. It is possible by this method to selectively obtain only 1224 without the generation of 1,2-dichloro-3,3,3-trifluoropropene (1233) as the by-product.

DESCRIPTION OF EMBODIMENTS

Hereinafter, the present invention will be described in detail below.

The production method of 1224 according to the present invention (hereinafter referred to as "present production method") includes the step of bringing 2,3-dichloro-1,1,1,3-tetrafloropropane (234da) into contact with the inorganic base having a pKa of 4.8 or greater in the aqueous medium in the presence of the phase transfer catalyst. In the present production method, the term "organic base" refers to any basic compound selected from primary, secondary and tertiary amines and nitrogen-containing heterocyclic compounds; and the term "inorganic base" refers to any basic compound other than the organic base.

[Inorganic Base]

As the inorganic base, there can be used a hydroxide, carbonate, hydrogencarbonate, phosphate or acetate of an alkali metal such as lithium, sodium or potassium, a hydroxide of an alkaline earth metal such as calcium and the like in the present production method. Specific examples of the inorganic base are sodium hydroxide, potassium hydroxide, calcium hydroxide, lithium carbonate, lithium hydrogencarbonate, lithium phosphate, sodium carbonate, sodium hydrogencarbonate, sodium phosphate, potassium carbonate, potassium hydrogencarbonate, potassium phosphate, lithium acetate, sodium formate, sodium acetate, potassium formate and potassium acetate.

In the present production method, the reaction rate of conversion of 234da to 1224 becomes lowered with the use of the inorganic base whose conjugate acid has an acid dissociation constant pKa of smaller than 4 (pKa<4). The reaction does not almost proceed with the use of potassium dihydrogenphosphate ($KH_2PO_4$) whose conjugate acid has an acid dissociation constant of 2 (pKa=2). However, the reaction proceeds favorably with the use of e.g. potassium acetate (AcOK) of pKa=4.8 or potassium hydrogen phosphate ($K_2HPO_4$) of pKa=7.2. The reaction proceeds at a high reaction rate and can be completed to increase the yield of 1224 with the use of e.g. potassium carbonate ($K_2CO_3$) or potassium phosphate ($K_3PO_4$), each of which has a pKa of 10 or greater. The reaction rate becomes particularly high with the use of e.g. sodium hydroxide (NaOH) or potassium hydroxide (KOH), each of which has a pKa of 15 or greater. In view of such a high reaction rate as well as high availability and low cost, these inorganic bases are preferred in the present production method.

In this way, the pKa of the inorganic base is preferably 4.8 or greater, more preferably 7 or greater, still more preferably 10 or greater, most preferably 15 or greater, in the present production method. In particular, the reaction proceeds quickly when the inorganic base used has a pKa of 10 or greater. The pKa values of the above inorganic bases are listed in e.g. "Chemical Handbook, Revised Fifth Edition, edited by the Chemical Society of Japan". The term "acid dissociation constant (pKa)" refers to a constant that comparatively expresses the proton-donating ability of a Brønsted acid against a water molecule as a standard proton acceptor. In the present production method, the alkaline strength of the inorganic base is expressed by the acid dissociation constant (pKa) of the conjugate acid.

The amount of the inorganic base used in the present production method is preferably 1 to 2 equivalents, more preferably 1 to 1.5 equivalents, per 1 equivalent of 234da used as the raw material. If the inorganic base is used in an amount of more than 2 equivalents, there may occur side reaction. The reaction may not be completed if the inorganic base is used in an amount of less than 1 equivalent.

As the inorganic base is generally solid, it is common practice to use the inorganic base by dissolving in a solvent. There can suitably be used a polar organic solvent or water as the solvent to dissolve the inorganic base. In the present production method, the formation reaction of 1224 is preferably performed in the aqueous medium in which the inorganic base is highly soluble. The concentration of the inorganic base in the aqueous medium is preferably 5 to 40 mass %. If the concentration of the inorganic base is lower than 5 mass %, the inorganic base has to be used in a more than necessary amount. The use of such more than necessary inorganic acid results in a deterioration of production efficiency. If the concentration of the inorganic base is higher than 40 mass %, the inorganic base or its salt may be precipitated in the reaction system. The occurrence of such a precipitate results in poor stirring during the reaction or complicated wastewater treatment after the reaction. The concentration of the inorganic base in the aqueous medium is more preferably 10 to 30 mass %.

[Organic Base]

In the present production method, it is feasible to use an organic base as an optional component in addition to the inorganic base. As the organic base, there can be used an alkali metal salt of a carboxylic acid of 1 to 6 carbon atoms or a tertiary amine of 3 to 18 carbon atoms. Specific examples of the tertiary amine are trimethylamine, triethylamine, tri-n-propylamine, triisopropylamine, tri-n-butylamine, triisobutylamine, tri-sec-butylamine, tri-tert-butylamine, tri-n-amylamine, triisoamylamine, tri-sec-amylamine, tri-tert-amylamine, N,N,N',N'-tetramethylethylenediamine, N,N,N',N'-tetramethylpropane-1,3-diamine, tetramethylguanidine, N-methyldiethylamine, N-methyldi-n-propylamine, N-methylisopropylamine, N-methyldi-n-butylamine, N-methyldiisobutylamine, N-methyldi-tert-butylamine, N,N-diisopropylbutylamine, N,N-dimethyl-n-octylamine, N,N-dimethylnonylamine, N,N-dimethyldecylamine, N,N-dimethylundecylamine, N,N-dimethyldodecylamine, N-methyldihexylamine. There can also be used a cyclic amine such as tetramethylguanidine, N,N'-dimethylpiperazine, 1,8-diazabicyclo[5.4.0]-7-undecene (DBU), 1,4-diazabicyclo[2.2.2]octane (DABCO) or bis(2-dimethylaminoethyl)ether.

The organic base is soluble in water and is converted to a salt by neutralization during wastewater treatment after the completion of the reaction. It is often the case that this organic salt needs to be recovered. The present production method enables selective and efficient production of 1224 from 234da, without by-production of 1223, by the use of the inorganic base in combination with a small amount of the phase transfer catalyst. The organic base may thus not be used, in addition to the inorganic base, unless necessary. In the case of using the organic base, the amount of the organic base used is preferably 0.5 equivalent or less, more preferably 0.1 equivalent or less, per 1 equivalent of 234da as the raw material of 1224. The inorganic base is neutralized after the completion of the reaction and easily processed as a water-soluble neutralized salt by wastewater treatment. When the organic base is neutralized, by contrast, the resulting neutralized organic base salt is not easy to remove from the reaction system and becomes a cause of processing load in mass-scale production.

[Phase Transfer Catalyst]

As mentioned above, the present production method is characterized by high-yield production of 1224, without by-production of 1223, by contact of 234da with the inorganic base in the presence of the phase transfer catalyst. The term "phase transfer catalyst" herein refers to a small amount of reagent used to react a water-insoluble organic compound with an organic solvent-insoluble reagent. In the present invention, the phase transfer catalyst specifically refers to a compound (a small amount of reagent) used to promote contact of 234da as the organic reactant material with the inorganic base in the aqueous medium.

As the phase transfer catalyst, there can suitably be used a quaternary ammonium salt, a crown ether, a calixarene, a cyclophane, a cyclodextrin, a pyridinium compound or the like. Among others, a quaternary ammonium salt is preferred. More preferred is a quaternary ammonium salt of 8 to 50 carbon atoms. For example, it is preferable in the present production method to use a fluoride, chloride, bromide or iodide of tetraethylammonium having 8 carbon atoms in total, tetrabutylammonium having 16 carbon atoms in total or methyltri-n-octylammonium having 25 carbon atoms in total as the phase transfer catalyst because these catalysts are readily available and, even in a small amount, exert a large effect of suppressing the generation of 1233 as the by-product. The above phase transfer catalysts can be used in any mixture thereof. It is particularly preferable to use any of tetrabutylammonium bromide, methyltri-n-octylammonium chloride, benzyltrimethylammonium chloride and tetraethylammonium chloride, each of which is readily available and exerts its effect even in a small amount, as the phase transfer catalyst in the present production method.

The amount of the phase transfer catalyst used in the present production method is preferably 0.01 to 10 mol % based on the total amount of 234da. If the phase transfer catalyst is used in an amount of less than 0.01 mol %, a sufficient effect may not be obtained. A further effect cannot be expected even if the phase transfer catalyst is used in an amount of more than 10 mol %. The use of such excessive phase transfer catalyst results in not only an increase of waster of the phase transfer catalyst but also an increase of complicated operation such as reactor cleaning after the completion of the reaction. There is thus no need to use more than 10 mol % of the phase transfer catalyst.

It is feasible to use a water-soluble organic compound, which is capable of dissolving both of 234da and water, in order to promote contact of 234da with the inorganic base in the aqueous medium. As the water-soluble organic compound, preferred is an organic substance that, when mixed with water at a volume ratio of 1:1, does not become separated from water. Examples of the water-soluble organic compound are ketones such as acetone, ethers and amides. However, the water-soluble organic compound needs to be added in a large amount relative to 234da in the case where the water-soluble organic compound is intended to suppress dehydrofluorination and prevent by-production of 1223 during the formation of 1224 by dehydrochlorination of 234da with the inorganic base. In this case, the recovery and removal of the water-soluble organic compound after the reaction is complicated in operation.

In the presence of a small amount of the phase transfer catalyst in the reaction system, the target compound 1224 can be obtained with high yield even by the use of the inorganic base, which is low in cost and less in environmental load, in the present production method. Although the water-soluble organic compound can be added to the phase transfer catalyst as mentioned above, the necessity of coexistence of the water-soluble organic compound is low in the present production method. It is rather preferable to perform the reaction without the coexistence of the water-soluble organic compound.

[Reaction Conditions]

In the present production method, the formation reaction of 1244 from 234da is performed in the aqueous medium. Any medium other than water can be added into the reaction system as long as the reaction proceeds favorably. However, the reaction proceeds favorably with the use of only water.

It suffices to bring 234da into contact with the inorganic base in the aqueous medium in the presence of the phase transfer catalyst at a temperature of −5° C. to 100° C. The contact temperature is preferably 0° C. to 50° C. If the contact temperature is lower than −5° C., the reaction rate is low so that it takes time to obtain a sufficient amount of 1224. Further, the aqueous medium may be frozen under such low-temperature conditions. Although it is feasible to prevent freezing of the aqueous medium by adding an organic solvent etc., the addition of such an organic solvent may cause a difficulty of separation of 2-chloro-1,3,3,3-tetrafluoropropene (1224) as the target compound from the organic solvent etc. or an increase of waste. If the contact temperature exceeds 100° C., the by-product may be unfavorably generated by side reaction.

The formation reaction of 1224 can be performed by contact of 234da with the inorganic acid in the aqueous medium in the presence of the phase transfer catalyst under pressurized conditions, reduced pressure conditions or atmospheric pressure conditions. It is however preferable to adopt atmospheric pressure conditions for industrial-scale production, i.e., industrial production of 1224 at an industrial plant with simple equipment.

There exist diastereoisomers of 234da. The erythro isomer of 234da has a boiling point of 70° C.; and the threo isomer of 234da has a boiling point of 74° C. The cis isomer of 2-chloro-1,3,3,3-tetrafluoropropene (1224Z) has a boiling point of 17° C.; and the trans isomer of 2-chloro-1,3,3,3-tetrafluoropropene (1224E) has a boiling point of 23° C. In the case where the reaction is performed at a temperature higher than the boiling point of 1224Z or 1224E, it is preferable to adopt a pressurized reaction technique of e.g. placing 234da together with the phase transfer catalyst in a pressurized reactor and adding an aqueous solution of the inorganic base into the pressurized reactor by a metering pump or a reactive distillation technique of performing the reaction, while distilling out the reaction product, by dropping 234da into an aqueous solution of the inorganic base heated to a temperature higher than the boiling point of 1224 and lower than the boiling point of 234da. The reactive distillation technique allows high-yield production of the target compound by easy operation and thus can suitably be applied to the present production method. For example, the reactive distillation technique is preferably used under atmospheric pressure conditions by adding the phase transfer catalyst to 2,3-dichloro-1,1,1,3-tetrafluoropropane (234da), gradually dropping an aqueous solution of the inorganic base, which has been heated at 20° C. to 50 C, to the reaction mixture and stirring the reaction mixture while extracting 2-chloro-1,3,3,3-tetrafluoropropene (1224) generated as a low-boiling gas. As will be explained in Examples 1, 2 and 7 to 9 of the present specification, the reaction is properly completed with the use of sodium hydroxide or potassium hydroxide as the inorganic base.

It is feasible to separate 1224 into a cis isomer (1224Z) and a trans isomer (1224E) by subjecting the reaction product to ordinary operation such as water washing, drying, distillation, adsorption and purification as needed.

In the present invention, any other fraction separated from the target compound by distillation and purification can be reused as the raw reactant material, used as an intermediate for pharmaceutical and agrichemical products or a raw material for polymers, or used for any purpose upon isomerization, disproportionation etc.

[Preparation of 234da as Raw Material Compound]

In the present production method, there is no particular restriction on the process for preparation of 234da as the raw material of 1224. It is feasible to readily prepare 234da by photochlorination of 1234, which is commercially available as a cover gas of a magnesium melting furnace etc., as discussed in Non-Patent Publication 1. In the case where 234da is prepared by photochlorination of commercially available 1,3,3,3-tetrafluoropropene (1234), the starting material 1234 can be a cis isomer, a trans isomer or a mixture of cis and trans isomers. The conversion of 1234 to 234da may be performed by any process other than photochlorination, such as chlorination with the use of a radical initiator or a catalyst, although it is convenient to photochlorinate 1234 to 234da by irradiation with ultraviolet light from a high-pressure mercury-vapor lamp. As will be explained in Preparation Example "Preparation of 2,3-dichloro-1,1,1,3-tetrafluoropropane (234da)" of the present specification, 234da is prepared by photochlorination of trans-1,3,3,3-tetrafluoropropene (1234) at −78° C.

EXAMPLES

The present invention will be described in more detail below by way of the following examples. It should be understood that the following examples are illustrative and are not intended to limit the present invention thereto. In the following examples, the compositions of organic substances were measured with a gas chromatograph (GC) using a hydrogen flame ionization detector (FID) and indicated by area % of the resulting GC record as "GC %" unless otherwise specified.

Preparation Example

Preparation of
2,3-dichloro-1,1,1,3-tetrafluoropropane (234da)

Provided was a 2000-ml glass reactor with a gas introduction hole. The bottom of the reactor was immersed and cooled in a dry ice/acetone bath of −78° C. Next, 901.86 g (7.90 mol) of trans-1,3,3,3-tetrafluoropropene as a starting material was placed into the reactor. The reaction was initiated by blowing chlorine ($Cl_2$) into the reactor at 1.70 g/min while keeping the reactor immersed in the acetone bath. The starting material and chlorine inside the reactor were stirred by a magnetic stirrer under the condition that the reactor was externally irradiated with ultraviolet light from a high-pressure mercury-vapor lamp. After the stirring for 5 hours and 30 minutes, the reaction was completed. The total introduction amount of the chlorine was 560.5 g (7.90 mol). The content of the reactor was washed with water, washed with a saturated aqueous solution of sodium hydrogencarbonate and then washed with a saturated solution of sodium chloride, thereby yielding a reaction product (1427.0 g) containing 234da as a target product compound. The composition of the reaction product was analyzed by gas chromatography. It was confirmed by gas chromatographic analysis that: the content of 234a was 98.7 GC %; and the yield of 234da was 96.3%.

Example 1

Into a 1-L four-neck flask with a Dimroth condenser, a 500-ml dropping funnel, a thermometer and a magnetic stirrer, 2.00 g (0.006 mol) of tetrabutylammonium bromide (TABA) as a phase transfer catalyst, 555.14 g (3.00 mol) of 234da prepared in Preparation Example were placed. The bottom of the flask was immersed in an ice water bath of 0 to 5° C. Stirring of the content of the flask was started while refluxing the content of the flask with flow of a coolant of −15° C. through the Dimroth condenser. Then, 504.47 g (3.15 mol) of a 25 mass % aqueous solution of sodium hydroxide (NaOH, pKa=15 or greater) was gradually dropped into the flask through the dropping funnel over 132 minutes. The content of the flask was stirred for 1 hour at the same temperature as above. After that, the flask was cooled in an ice water bath until the inside temperature of the flask became 5° C. or lower. The Dimroth condenser and the dropping funnel was detached from the flask. Instead, a simple distillation unit with a 30-cm Vigreux column was attached to the flask. The content of the flask was subjected to distillation by the distillation unit. With this, 424.87 g of a reaction product containing 1224 was recovered. The composition of the reaction product was analyzed by gas chromatography. It was confirmed by gas chromatographic analysis that: the content of 2-chloro-1,3,3,3-tetrafluoropropene (1224) was 96.23 GC %; the content of dichloro-3,3,3-trifluoropropene (1223) was 3.23 GC %; and the content of unreacted 234da was 0.02 GC %.

Example 2

Into a 100-ml four-neck flask with a Dimroth condenser, a 100-ml dropping funnel, a thermometer and a magnetic stirrer, 0.44 g (0.0014 mol) of tetrabutylammonium bromide (TABA) as a phase transfer catalyst and 25.15 g (0.14 mol) of 234da prepared in Preparation Example were placed. The bottom of the flask was immersed in an ice water bath of 0 to 5° C. Stirring of the content of the flask was started with flow of a coolant of −15° C. through the Dimroth condenser. Then, 33.50 g (0.15 mol) of a 25 mass % aqueous solution of potassium hydroxide (KOH, pKa=15 or greater) was gradually dropped into the flask through the dropping funnel over 60 minutes. The content of the flask was stirred for 1 hour at the same temperature as above. After that, the flask was cooled in an ice water bath until the inside temperature of the flask became 5° C. or lower. The content of the flask was transferred to a 100-ml separating funnel, which had been cooled in advance in a refrigerator, and subjected to two-phase separation. With this, 19.41 g of an organic phase containing 1224 was recovered as a reaction product. The composition of the organic phase was analyzed by gas chromatography. It was confirmed by gas chromatographic analysis that: the content of 1224 was 95.21 GC %; the content of 1223 was 3.12 GC %; and the content of unreacted 234da was 0.01 GC %.

Example 3

Into a 200-ml four-neck flask with a Dimroth condenser, a 200-ml dropping funnel, a thermometer and a magnetic stirrer, 0.42 g (0.0013 mol) of tetrabutylammonium bromide (TABA) as a phase transfer catalyst and 25.29 g (0.14 mol) of 234da prepared in Preparation Example were placed. The bottom of the flask was immersed in a water bath of 15 to 20° C. Stirring of the content of the flask was started with flow of a coolant of −15° C. through the Dimroth condenser. Then, 127.48 g (0.15 mol) of a 25 mass % aqueous solution of tripotassium phosphate ($K_3PO_4$, pKa=13) was gradually dropped into the flask through the dropping funnel over 102 minutes. The content of the flask was stirred for 3 hours at the same temperature as above. After that, the flask was cooled in an ice water bath until the inside temperature of the flask became 5° C. or lower. The content of the flask was transferred to a 200-ml separating funnel, which had been cooled in advance in a refrigerator, and subjected to two-phase separation. With this, 21.20 g of an organic phase containing 1224 was recovered as a reaction product. The composition of the organic phase was analyzed by gas chromatography. It was confirmed by gas chromatographic analysis that: the content of 1224 was 90.52 GC %; the content of 1223 was 3.23 GC %; and the content of unreacted 234da was 5.01 GC %.

Example 4

Into a 200-ml four-neck flask with a Dimroth condenser, a 200-ml dropping funnel, a thermometer and a magnetic stirrer, 0.40 g (0.0012 mol) of tetrabutylammonium bromide (TABA) as a phase transfer catalyst and 25.48 g (0.14 mol) of 234da prepared in Preparation Example were placed. The bottom of the flask was immersed in a water bath of 15 to 20° C. Stirring of the content of the flask was started with flow of a coolant of −15° C. through the Dimroth condenser. Then, 104.68 g (0.15 mol) of a 25 mass % aqueous solution of dipotassium hydrogenphosphate ($K_2HPO_4$, pKa=7.2) was gradually dropped into the flask through the dropping funnel over 62 minutes. The content of the flask was stirred for 2 hours at the same temperature as above. After that, the flask was cooled in an ice water bath until the inside temperature of the flask became 5° C. or lower. The content of the flask was transferred to a 200-ml separating funnel, which had been cooled in advance in a refrigerator, and subjected to two-phase separation. With this, 21.51 g of an organic phase containing 1224 was recovered as a reaction product. The composition of the organic phase was analyzed by gas chromatography. It was confirmed by gas chromatographic analysis that: the content of 1224 was 14.06 GC %; the content of 1223 was 0.00 GC %; and the content of unreacted 234da was 84.35 GC %.

Example 5

Into a 100-ml four-neck flask with a Dimroth condenser, a 100-ml dropping funnel, a thermometer and a magnetic stirrer, 0.44 g (0.0014 mol) of tetrabutylammonium bromide (TABA) as a phase transfer catalyst and 25.15 g (0.14 mol) of 234da prepared in Preparation Example were placed. The bottom of the flask was immersed in a water bath of 15 to 20° C. Stirring of the content of the flask was started with flow of a coolant of −15° C. through the Dimroth condenser. Then, 58.70 g (0.15 mol) of a 25 mass % aqueous solution of potassium acetate (AcOK, pKa=4.8) was gradually dropped into the flask through the dropping funnel over 60 minutes. The content of the flask was stirred for 1 hour at the same temperature as above. After that, the flask was cooled in an ice water bath until the inside temperature of the flask became 5° C. or lower. The content of the flask was transferred to a 200-ml separating funnel, which had been cooled in advance in a refrigerator, and subjected to two-phase separation. With this, 24.42 g of an organic phase containing 1224 was recovered as a reaction product. The composition of the organic phase was analyzed by gas chromatography. It was confirmed by gas chromatographic analysis that: the content of 1224 was 8.25 GC %; the content of 1223 was 0.01 GC %; and the content of unreacted 234da was 89.36 GC %.

Example 6

Into a 50-ml autoclave of glass with a pressure gauge and a valve, 0.17 g (0.0005 mol) of tetrabutylammonium bromide (TABA) as a phase transfer catalyst was placed. A vacuum pump was connected to the autoclave. After the autoclave was evacuated by the vacuum pump, the valve of the autoclave was closed. The bottom of the autoclave was immersed and cooled in an ice water bath. The valve of the autoclave was opened upon connection of a tube of tetrafluoroetylene-perfluoroalkylvinylether copolymer (hereinafter sometimes referred to as "PFA") to the valve. Then, 10.00 g (0.05 mol) of 234da prepared in Preparation Example was fed into the autoclave. Subsequently, 43.10 g (0.06 mol) of a 25 mass % aqueous solution of dipotassium hydrogenphosphate ($K_2HPO_4$, pKa=7.2) was fed into the autoclave. After that, the valve of the autoclave was closed. The content of the autoclave was stirred for 30 minutes at room temperature (25° C.). The bottom of the autoclave was immersed in an oil bath of 50° C. In this state, the content of the autoclave was reacted by stirring for 3 hours. During the reaction, the reading of the pressure gauge was 0.12 MPaG. The content of the autoclave was transferred to a separating funnel, which had been cooled in advance in a refrigerator, and subjected to two-phase separation. With this, 7.98 g of an organic phase was recovered. The composition of the organic phase was analyzed by gas chromatography. It was confirmed by gas chromatographic analysis that: the content of 1224 was 66.21 GC %; the content of 1223 was 0.05 GC %; and the content of unreacted 234da was 32.53 GC %.

Example 7

Into a 100-ml four-neck flask with a Dimroth condenser, a 100-ml dropping funnel, a thermometer and a magnetic stirrer, 0.0014 mol of methyltri-n-octylammonium chloride as a phase transfer catalyst and 25.15 g (0.14 mol) of 234da prepared in Preparation Example were placed. The bottom of the flask was immersed in an ice water bath of 0 to 5° C. Stirring of the content of the flask was started with flow of a coolant of −15° C. through the Dimroth condenser. Then, 33.50 g (0.15 mol) of a 25 mass % aqueous solution of potassium hydroxide (KOH, pKa=15 or greater) was gradually dropped into the flask through the dropping funnel over 60 minutes. The content of the flask was stirred for 1 hour at the same temperature as above. After that, the flask was cooled in an ice water bath until the inside temperature of the flask became 5° C. or lower. The content of the flask was transferred to a 100-ml separating funnel, which had been cooled in advance in a refrigerator, and subjected to two-phase separation. With this, an organic phase containing 1224 was recovered as a reaction product. The composition of the organic phase was analyzed by gas chromatography. It was confirmed by gas chromatographic analysis that: the content of 1224 was 95.12 GC %; the content of 1223 was 3.34 GC %; and the content of unreacted 234da was 0.06 GC %.

Example 8

Into a 100-ml four-neck flask with a Dimroth condenser, a 100-ml dropping funnel, a thermometer and a magnetic stirrer, 0.0014 mol of benzyltrimethylammonium chloride as a phase transfer catalyst and 25.15 g (0.14 mol) of 234da prepared in Preparation Example were placed. The bottom of the flask was immersed in an ice water bath of 0 to 5° C. Stirring of the content of the flask was started with flow of a coolant of −15° C. through the Dimroth condenser. Then, 33.50 g (0.15 mol) of a 25 mass % aqueous solution of potassium hydroxide (KOH, pKa=15 or greater) was gradually dropped into the flask through the dropping funnel over 60 minutes. The content of the flask was stirred for 1 hour at the same temperature as above. After that, the flask was cooled in an ice water bath until the inside temperature of the flask became 5° C. or lower. The content of the flask was transferred to a 100-ml separating funnel, which had been cooled in advance in a refrigerator, and subjected to two-phase separation. With this, an organic phase containing 1224 was recovered as a reaction product. The composition of the organic phase was analyzed by gas chromatography. It was confirmed by gas chromatographic analysis that: the content of 1224 was 95.09 GC %; the content of 1223 was 3.28 GC %; and the content of unreacted 234da was 0.08 GC %.

Example 9

Into a 100-ml four-neck flask with a Dimroth condenser, a 100-ml dropping funnel, a thermometer and a magnetic stirrer, 0.0014 mol of tetraethylammonium chloride as a phase transfer catalyst and 25.15 g (0.14 mol) of 234da prepared in Preparation Example were placed. The bottom of the flask was immersed in an ice water bath of 0 to 5° C. Stirring of the content of the flask was started with flow of a coolant of −15° C. through the Dimroth condenser. Then, 33.50 g (0.15 mol) of a 25 mass % aqueous solution of potassium hydroxide (KOH, pKa=15 or greater) was gradually dropped into the flask through the dropping funnel over 60 minutes. The content of the flask was stirred for 1 hour at the same temperature as above. After that, the flask was cooled in an ice water bath until the inside temperature of the flask became 5° C. or lower. The content of the flask was transferred to a 100-ml separating funnel, which had been cooled in advance in a refrigerator, and subjected to two-phase separation. With this, an organic phase containing 1224 was recovered as a reaction product. The composition of the organic phase was analyzed by gas chromatography. It was confirmed by gas chromatographic analysis that: the content of 1224 was 94.98 GC %; the content of 1223 was 3.09 GC %; and the content of unreacted 234da was 0.07 GC %.

Comparative Example 1

Into a 100-ml four-neck flask with a Dimroth condenser, a 100-ml dropping funnel, a thermometer and a magnetic stirrer, 25.03 g (0.14 mol) of 234da prepared in Preparation Example was placed. The bottom of the flask was immersed in an ice water bath of 0 to 5° C. Stirring of the content of the flask was started with flow of a coolant of −15° C. through the Dimroth condenser. Then, 33.40 g (0.15 mol) of a 25 mass % aqueous solution of potassium hydroxide (KOH, pKa=15 or greater) was gradually dropped into the flask through the dropping funnel over 68 minutes. The content of the flask was stirred for 2 hours at the same temperature as above. After that, the flask was cooled in an ice water bath until the inside temperature of the flask reached 5° C. or lower. The content of the flask was transferred to a 100-ml separating funnel, which had been cooled in advance in a refrigerator, and subjected to two-phase separation. With this, 21.75 g of an organic phase containing 1224 was recovered as a reaction product. The composition of the reaction product was analyzed by gas chromatography. It was confirmed by gas chromatographic analysis that: the content of 1224 was 68.11 GC %; the content of 1223 was 25.39 GC %; and the content of unreacted 234da was 5.37 GC %. Without the use of a phase transfer catalyst, there was generated a large amount of 1223 as a by-product.

Comparative Example 2

Into a 50-ml autoclave of glass with a pressure gauge and a valve, 0.13 g (0.0004 mol) of tetrabutylammonium bromide (TABA) was placed. A vacuum pump was connected to the autoclave. After the autoclave was evacuated by the vacuum pump, the valve of the autoclave was closed. The bottom of the autoclave was immersed and cooled in an ice water bath. The valve of the autoclave was opened upon connection of a PFA tube to the valve. Then, 7.51 g (0.06 mol) of 234da prepared in Preparation Example was fed into the autoclave. Subsequently, 42.01 g (0.06 mol) of a 20 mass % aqueous solution of potassium dihydrogenphosphate ($KH_2PO_4$, pKa=2) was fed into the autoclave. After that, the valve of the autoclave was closed. The content of the autoclave was stirred for 30 minutes at room temperature (25° C.). The bottom of the autoclave was immersed in an oil bath of 50° C. In this state, the content of the autoclave was reacted by stirring for 3 hours. During the reaction, the reading of the pressure gauge was 0.03 MPaG. The content of the autoclave was transferred to a separating funnel, which had been cooled in advance in a refrigerator, and subjected to two-phase separation. With this, 6.81 g of an organic phase was recovered as a reaction product. The composition of the organic phase was analyzed by gas chromatography. It was confirmed by gas chromatographic analysis that: the content of 1224 was 1.15 GC %; the content of 1223 was 0.00 GC %; and the content of unreacted 234da was 97.62 GC %. With the use of the aqueous solution of potassium dihydrogenphosphate having a pKa of 2.0, the reaction did not proceed because of too small pKa value.

The results of Examples 1 to 9 and Comparative Examples 1 and 2 are summarized in TABLE 1.

TABLE 1

| Example No. | Kind of base | pKa of base | Phase transfer catalyst | Composition (GC %) | | | |
|---|---|---|---|---|---|---|---|
| | | | | 1224 | 1223 | 234da | others |
| Example 1 | NaOH | 15 or greater | TABA | 96.23 | 3.23 | 0.02 | 0.43 |
| Example 2 | KOH | 15 or greater | TABA | 95.21 | 3.12 | 0.01 | 1.66 |
| Example 3 | $K_3PO_4$ | 13 | TABA | 90.52 | 3.23 | 5.01 | 1.24 |
| Example 4 | $K_2HPO_4$ | 7.2 | TABA | 14.06 | 0.00 | 84.35 | 1.59 |
| Example 5 | AcOK | 4.8 | TABA | 8.25 | 0.01 | 89.36 | 2.38 |
| Example 6 | $K_2HPO_4$ | 7.2 | TABA | 66.21 | 0.05 | 32.54 | 1.20 |
| Example 7 | KOH | 15 or greater | X | 95.12 | 3.34 | 0.06 | 1.48 |
| Example 8 | KOH | 15 or greater | Y | 95.09 | 3.28 | 0.08 | 1.55 |
| Example 9 | KOH | 15 or greater | Z | 94.98 | 3.09 | 0.07 | 1.86 |
| Comparative Example 1 | KOH | 15 or greater | none | 68.11 | 25.39 | 5.37 | 1.13 |
| Comparative Example 2 | $KH_2PO_4$ | 2 | TABA | 1.15 | 0.00 | 97.62 | 1.23 |

Phase transfer catalyst
TABA: tetrabutylammonium bromide
X: methyltri-n-octylammonium chloride
Y: benzyltrimethylammonium chloride
Z: tetraethylammonium chloride

The invention claimed is:

1. A production method of 2-chloro-1,3,3,3-tetrafluoropropene, comprising: bringing 2,3-dichloro-1,1,1,3-tetrafluoropropane into contact with either sodium hydroxide or potassium hydroxide as an inorganic base in an aqueous medium in the presence of at least one kind of phase transfer catalyst selected from the group consisting of tetrabutylammonium bromide, methyltri-n-octylammonium chloride, benzyltrimethylammonium chloride and tetraethylammonium chloride.

2. The production method according to claim 1, wherein the inorganic base is used in an amount of 1 to 2 equivalents per 1 equivalent of the 2-chloro-1,3,3,3-tetrafluoropropene.

3. The production method according to claim 2, wherein the inorganic base is used in an amount of 1 to 1.5 equivalents per 1 equivalent of the 2-chloro-1,3,3,3-tetrafluoropropene.

4. The production method according to claim 1, wherein the at least one kind of phase transfer catalyst is used in an amount of 0.01 to 10 mol % based on the total amount of the 2-chloro-1,3,3,3-tetrafluoropropene.

5. The production method according to claim 1, wherein the 2,3-dichloro-1,1,1,3-tetrafluoropropane is brought into contact with the inorganic base at a contact temperature of −5° C. to 100° C.

6. The production method according to claim 5, wherein the contact temperature is 0° C. to 50° C.

7. The production method according to claim 1,
wherein the inorganic base is used in an amount of 1 to 2 equivalents per 1 equivalent of the 2-chloro-1,3,3,3-tetrafluoropropene;
wherein the at least one kind of phase transfer catalyst is used in an amount of 0.01 to 10 mol % based on the total amount of the 2-chloro-1,3,3,3-tetrafluoropropene; and
wherein the 2,3-dichloro-1,1,1,3-tetrafluoropropane is brought into contact with the inorganic base at a contact temperature of 0° C. to 50° C.

* * * * *